United States Patent [19]

Mancuso et al.

[11] Patent Number: 6,150,525
[45] Date of Patent: Nov. 21, 2000

[54] PYRROLO [3,2-B]PYRIDINE PROCESSES AND INTERMEDIATES

[75] Inventors: Vincent Mancuso, They-le-Chateau; Freddy Andre Napora, Gembloux, both of Belgium; Uko Effiong Udodong, Indianapolis; Daniel Edward Verral, II, Clinton, both of Ind.

[73] Assignee: Eli Lilly and Company, Indianapolis, Ind.

[21] Appl. No.: 09/188,784

[22] Filed: Nov. 6, 1998

Related U.S. Application Data

[60] Provisional application No. 60/065,853, Nov. 14, 1997.

[51] Int. Cl.$^7$ .................................................. C07D 471/04
[52] U.S. Cl. ............................................................ 546/113
[58] Field of Search ............................................. 546/113

[56] References Cited

U.S. PATENT DOCUMENTS 5,521,196  5/1996  Audia et al. ........................... 514/323
5,521,197  5/1996  Audia et al. ........................... 514/323
5,817,671  6/1998  Filla et al. ............................. 546/113

*Primary Examiner*—Bernard Dentz
*Attorney, Agent, or Firm*—Robert D. Titus

[57] ABSTRACT

The present invention provides processes and intermediates of Formula I:

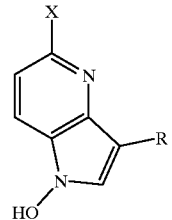

where X and R are defined in the specification, for the preparation of 5-amino-3-(1-methylpiperidin-4-yl)pyrrolo-[3,2-b]pyridine.

21 Claims, No Drawings

6,150,525

PYRROLO [3,2-B]PYRIDINE PROCESSES AND INTERMEDIATES

PRIORITY INFORMATION

This application claims priority of Provisional Application Serial No. 60/065,853 filed Nov. 14, 1997.

BACKGROUND OF THE INVENTION

This invention belongs to the fields of pharmaceutical chemistry and synthetic organic chemistry, and provides processes and key intermediates for the synthesis of N-[propionyl]-5-amino-3-(1-methylpiperidin-4-yl)pyrrolo[3,2-b]pyridine, a selective $5\text{-}HT_{1F}$ agonist.

Serotonin (5-HT) exhibits diverse physiological activity mediated by at least seven receptor classes, the most heterogeneous of which appears to be $5\text{-}HT_1$. A human gene which expresses one of these $5\text{-}HT_1$ receptor subtypes, named $5\text{-}HT_{1F}$, was isolated by Kao and coworkers (*Proc. Natl. Acad. Sci. USA*, 90, 408–412 (1993)). This $5\text{-}HT_{1F}$ receptor exhibits a pharmacological profile distinct from any serotonergic receptor yet described.

Moskowitz has proposed that currently unknown triggers for pain stimulate trigeminal ganglia which innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the $5\text{-}HT_{1D}$ subtype, located on the trigeminovascular fibers (*Neurology*, 43(suppl. 3), S16–S20 (1993)). It has been demonstrated that agonists of the $5\text{-}HT_{1F}$ receptor inhibit peptide extravasation due to stimulation of the trigeminal ganglia (Audia and Nissen, U.S. Pat. No. 5,521,196).

Compounds which exhibit affinity for the $5\text{-}HT_{1F}$ receptor provide a new approach for the treatment of diseases linked to abnormal serotonergic neurotransmission. Furthermore, compounds selective for the $5\text{-}HT_{1F}$ receptor subtype are potentially useful for treating such diseases while causing fewer undesired side effects. N-[propionyl]-5-amino-3-(1-methylpiperidin-4-yl)pyrrolo[3,2-b]pyridine is a selective $5\text{-}HT_{1F}$ agonist which may be prepared by acylation of 5-amino-3-(1-methylpiperidin-4-yl)pyrrolo[3,2-b]pyridine.

BRIEF SUMMARY OF THE INVENTION

The present invention provides a process for the preparation of 5-amino-3-(1-methylpiperidin-4-yl)pyrrolo-[3,2-b]pyridine (A), comprising the steps of:
 i) condensing 1-hydroxy-5-(dimethylaminomethyleneimino)pyrrolo[3,2-b]pyridine (F) with 1-methyl-4-piperidinone in the presence of a base to provide 1-hydroxy-5-(dimethylaminomethyleneimino)-3-(1-methyl-1,2,3,6-tetrahydropyridin-4-yl)pyrrolo[3,2-b]pyridine (J);
 ii) optionally deprotecting (J) to provide 1-hydroxy-5-amino-3-(1-methyl-1,2,3,6-tetrahydropyridin-4-yl)pyrrolo-[3,2-b]pyridine (H); and
 iii) hydrogenating either (J) or (H).

The present invention also provides a process for the preparation of 5-amino-3-(1-methylpiperidin-4-yl)pyrrolo-[3,2-b]pyridine (A) comprising the steps of:
 i) condensing 1-hydroxy-5-aminopyrrolo[3,2-b]pyridine (G) with 1-methyl-4-piperidinone in the presence of a base to provide 1-hydroxy-5-amino-3-(1-methyl-1,2,3,6-tetrahydro-pyridin-4-yl)pyrrolo[3,2-b]pyridine (H); and
 ii) hydrogenating (H).

The present invention additionally provides a process for the preparation of 5-amino-3-(1-methylpiperidin-4-yl)pyrrolo-[3,2-b]pyridine (A), comprising the steps of:
 i) nitrating 6-amino-2-picoline to provide a mononitrated 6-amino-2-picoline consisting of a mixture of 3-nitro- and 5-nitro-6-amino-2-picoline (B);
 ii) optionally separating the mixture of 3-nitro- and 5-nitro-6-amino-2-picoline (B) to provide a mononitrated 6-amino-2-picoline consisting of substantially pure 3-nitro-6-amino-2-picoline (C);
 iii) reacting a mononitrated 6-amino-2-picoline selected from (B) or (C) with a dimethylaminoformylating agent to provide 2-(2-dimethylaminoethen-1-yl)-3-nitro-6-(dimethylaminomethyleneimino)pyridine (E); and
 iv) hydrogenating (E) in the presence of acid to provide 1-hydroxy-5-dimethylamino-methyleneiminopyrrolo[3,2-b]pyridine (F);
 v) reacting (F) with 1-methyl-4-piperidinone in the presence of a base to provide 1-hydroxy-5-(dimethylaminomethyleneimino)-3-(1-methyl-1,2,3,6-tetrahydropyridin-4-yl)pyrrolo[3,2-b]pyridine (J);
 vi) optionally deprotecting (J) to provide 1-hydroxy-5-amino-3-(1-methyl-1,2,3,6-tetrahydropyridin-4-yl)pyrrolo-[3,2-b]pyridine (H); and
 vii) hydrogenating either (J) or (H).

A further embodiment of the present invention is a process for the preparation of N-[propionyl]-5-amino-3-(1-methylpiperidin-4-yl)pyrrolo[3,2-b]pyridine comprising the acylation of 5-amino-3-(1-methylpiperidin-4-yl)pyrrolo[3,2-b]pyridine (A) prepared by any of the previously described processes.

The present invention also provides a process for the preparation of 1-hydroxy-5-dimethylaminomethyleneiminopyrrolo[3,2-b]pyridine (F), comprising the steps of:
 i) nitrating 6-amino-2-picoline to provide a mononitrated 6-amino-2-picoline consisting of a mixture of 3-nitro- and 5-nitro-6-amino-2-picoline (B);
 ii) optionally separating the mixture of 3-nitro- and 5-nitro-6-amino-2-picoline (B) to provide a mononitrated 6-amino-2-picoline consisting of substantially pure 3-nitro-6-amino-2-picoline (C);
 iii) reacting a mononitrated 6-amino-2-picoline selected from (B) or (C) with a dimethylaminomethylating agent to provide 2-(2-dimethylaminoethen-1-yl)-3-nitro-6-(dimethylaminomethyleneimino)pyridine (E); and
 iv) hydrogenating (E) in the presence of acid.

Furthermore, the present invention provides 1-hydroxypyrrolo[3,2-b]pyridines of Formula I:

I

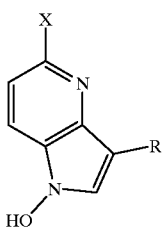

where:

X is amino or $(CH_3)_2NCH=N-$; and

R is hydrogen or 1-methyl-1,2,3,4-tetrahydropyridin-4-yl; and acid addition salts thereof.

DETAILED DESCRIPTION OF THE INVENTION

The intermediate 1-hydroxy-5-(dimethylaminomethyleneimino)pyrrolo[3,2-b]pyridine (F) is prepared beginning with 6-amino-2-picoline (6-amino-2-methylpyridine) by the procedure illustrated in Synthetic Scheme I.

The temperation of the solution of 6-amino-2-picoline prior to addition of the nitric acid solution is from about −15° C. to about −5° C. Preferably the temperature of this solution prior to addition of the nitric acid solution is from about −15° C. to about −10° C. It is especially preferred that the temperature of this solution is about −15° C. The nitric acid solution is added at a rate such that the temperature of the reaction mixture is maintained from about −15° C. to about 160° C. Preferably, the temperature of the reaction mixture is maintained at from about −15 20 C. to about ambient temperature during the addition of the nitric acid solution. It is more preferred that the temperature of the reaction mixture is maintained at from about −15° C. to about 0° C. during the addition of the nitric acid solution. It is especially preferred that the temperature of the reaction mixture is maintained from about −1° C. to about −2° C. during the addition of the nitric acid solution. It is also preferred that the nitric acid solution is precooled to about 0° C. prior to addition to the solution ot 6-amino-2-picoline.

Once the addition of the nitric acid solution is complete, the reaction mixture is allowed to warm gradually to room temperature, typically over about 2 hours, and is then stirred at room temperature for about 2 hours. It is preferred that the warming process is staged, maintaining the temperature of Synthetic Scheme I

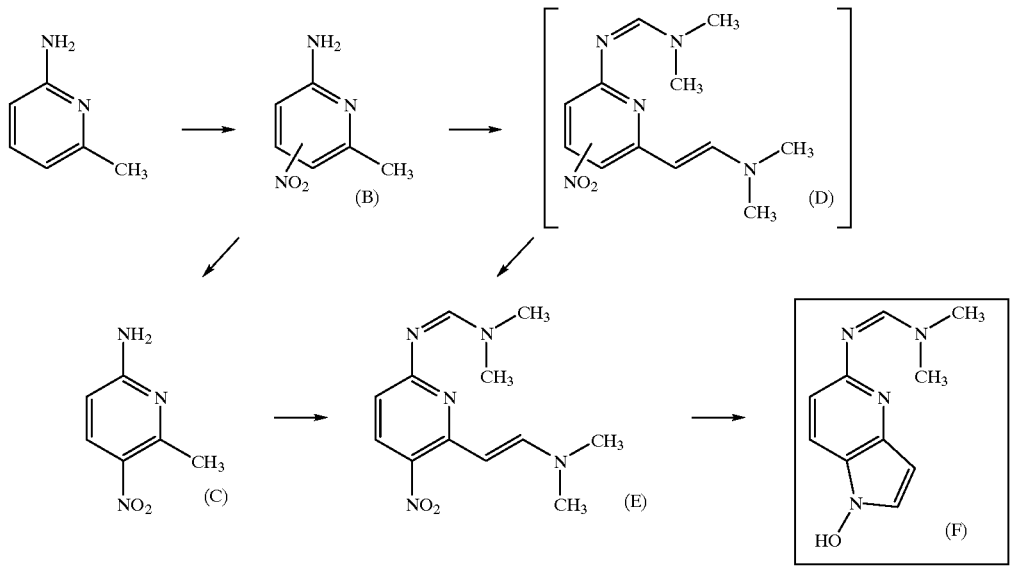

Preparation of mononitrated 6-amino-2-picoline

The nitration of 6-amino-2-picoline (6-amino-2-methylpyridine) may be performed by standard nitration methods (Parker and Shive, *Journal of the American Chemical Society*, 69, 63–67 (1947)). Preferably about 1 equivalent of concentrated nitric acid in about an equal volume of concentrated sulfuric is added to a solution of 6-amino-2-picoline in from about 2.5 to about 10 volumes of concentrated sulfuric acid relative to the volume of the nitric acid solution. It is especially preferred that the 6-amino-2-picoline is dissolved in about 5 volumes of concentrated sulfuric acid relative to the volume of the nitric acid solution.

the reaction mixture at from about −1 to 0° C. for about one hour after the addition is complete, warming the reaction mixture to about 10° C. over about one hour, maintaining the temperature of the reaction mixture at about 10° C. for about one hour, allowing the reaction mixture to warm to about 20° C. over about one hour, and maintaining the temperature of the reaction mixture at 20° C. for about one hour.

Once the reaction is complete, the pH of the reaction mixture is adjusted to at least 9 by the addition of base. Preferably, the reaction mixture is adjusted to a pH of about 9. The base may be any water soluble base capable of neutralizing the acid and adjusting the pH of the reaction mixture to the requisite level. Typically, the base is a hydroxide base such as lithium, potassium, sodium, or ammonium hydroxide. Preferably the base is ammonium hydroxide. The product (B) is typically isolated by standard techniques, preferably by filtration.

The nitration step provides a mixture, typically in the range of about 2:1 of 3-nitro-6-amino-2-picoline:5-nitro-6-amino-2-picoline. These isomers may be separated if desired to provide essentially pure 3-nitro-6-amino-2-picoline (C) prior to use in subsequent reactions.

The term "mononitrated 6-amino-2-picoline" as used in the present invention is taken to mean either a mixture of 3-nitro-6-amino-2-picoline and 5-nitro-6-amino-2-picoline, or essentially pure 3-nitro-6-amino-2-picoline.

The term "essentially pure 3-nitro-6-amino-2-picoline" as used in the present invention is taken to mean 3-nitro-6-amino-2-picoline containing from 0% to about 2% 5-nitro-6-amino-2-picoline.

Essentially pure 3-nitro-6-amino-2-picoline may be isolated from the mixture of nitration products by steam distillation as described by Parker and Shive supra. Alternatively, the 3-nitro isomer may be isolated by sublimation. Preferably, essentially pure 3-nitro-6-amino-2-picoline may be isolated from the mixture of mononitration isomers by recrystallization from a suitable solvent. Suitable solvents for recrystallization include methanol and toluene. The preferred recrystallization solvent is toluene.

Preparation of 2-(2-dimethylaminoethylen-1-yl)-3-nitro-6-(dimethylaminomethyleneimino)pyrrolo[3,2-b]pyridine (E)

Mononitrated 6-amino-2-picoline is reacted with a dimethylaminoformylating agent, typically dimethylformamide dimethylacetal or tris(dimethylamino)methane, in a suitable solvent, typically dimethylformamide. The reaction mixture is heated at about its reflux temperature for about two days, at which time the reaction mixture is cooled to ambient temperature.

Where the mononitrated 6-amino-2-picoline is essentially pure 3-nitro-6-amino-2-picoline (C), the product may be isolated by evaporation of dimethylformamide followed by multiple coevaporation cycles with toluene. Preferably the product is precipitated from the reaction mixture by the addition of about two volumes of isopropanol after the reaction mixture has cooled to ambient temperature.

Where the mononitrated 6-amino-2-picoline is a mixture of 3-nitro- and 5-nitro-6-amino-2-picoline (B) the cooled reaction mixture is poured into about 20 volumes of water at about 10° C. with vigorous stirring. After stirring for at least about 10 minutes, the reaction mixture is filtered to provide 2-(2-dimethylaminoethylen-1-yl)-3-nitro-6-(dimethylaminomethyleneimino)pyrrolo[3,2-b]pyridine (E).

It is preferred that the mononitrated 6-amino-2-picoline employed in the dimethylaminoformylation step is essentially pure 3-nitro-6-amino-2-picoline (C).

Hydrogenation

The 2-(2-dimethylaminoethylen-1-yl)-3-nitro-6-(dimethylaminomethyleneimino)pyrrolo[3,2-b]pyridine (E) is hydrogenated over a precious metal catalyst in the presence of acid to provide 1-hydroxy-5-(dimethylaminomethyleneimino)pyrrolo[3,2-b]pyridine (F). Substrate (E) is dissolved in a suitable solvent containing a precious metal catalyst. Suitable solvents include the lower alkanols such as methanol, ethanol, propanol and isopropanol, and mixtures thereof. Preferred solvents include methanol, ethanol, and mixtures thereof. Methanol and mixtures of methanol and ethanol are especially preferred solvents.

The skilled artisan will appreciate that a number of commonly used precious metal catalysts will be effective in the hydrogenation of substrate (E). Suitable catalysts include platinum and palladium. The preferred catalyst is palladium. Where the precious metal catalyst is palladium, it is preferred that the precious metal is supported on carbon. Typically, the carbon supported catalyst contains from about 5 to about 10% of palladium. It is especially preferred that the precious metal catalyst is 10% palladium on carbon.

Once the substrate has dissolved in the solvent, the reaction mixture is treated with from about two to about ten equivalents of acid. Any acid capable of sufficiently protonating the substrate without interfering with the formation of product is useful for the process of the present invention. Useful acids include, but are not limited to, trifluoroacetic acid, methanesulfonic acid, trifluoromethanesulfonic acid, hydrogen chloride, hydrogen bromide, and the like. It is preferred that the acid is hydrogen chloride. It is also preferred that from about 5 to about 10 equivalents of acid are added to the reaction mixture. It is especially preferred that about 9 to about 10 equivalents of acid are added to the reaction mixture.

The reaction mixture is then hydrogenated at an initial pressure of from about 10 to about 50 p.s.i. at an initial temperature of about ambient temperature, typically about 20° C. It is preferred that the initial hydrogen pressure is about 30 p.s.i. The reaction is exothermic and may range from the initial temperature of about 20° C. to about 40° C. It is preferred that the temperature range is maintained in the range of from about 20° C. to about 27° C.

After the hydrogenation is complete, the reaction mixture is diluted with ethanol and the solid product isolated under standard conditions such as filtration or centrifugation. The product may be separated from insoluble catalyst by recrystallization from a suitable solvent, preferably methanol. The product may be further purified by stirring in a mixture of methanol and ethanol in the presence of acid for about 4 hours at about ambient temperature. The 1-hydroxy-5-(dimethylaminomethyleneimino)pyrrolo[3,2-b]pyridine (F) is isolated by standard techniques, preferably by filtration or centrifugation.

The preparation of 5-amino-3-(1-methylpiperidin-4-yl)-pyrrolo[3,2-b]pyridine (A) beginning with 1-hydroxy-5-(dimethylaminomethyleneimino)pyrrolo[3,2-b]pyridine (F) is illustrated in Synthetic Scheme II.

Synthetic Scheme II

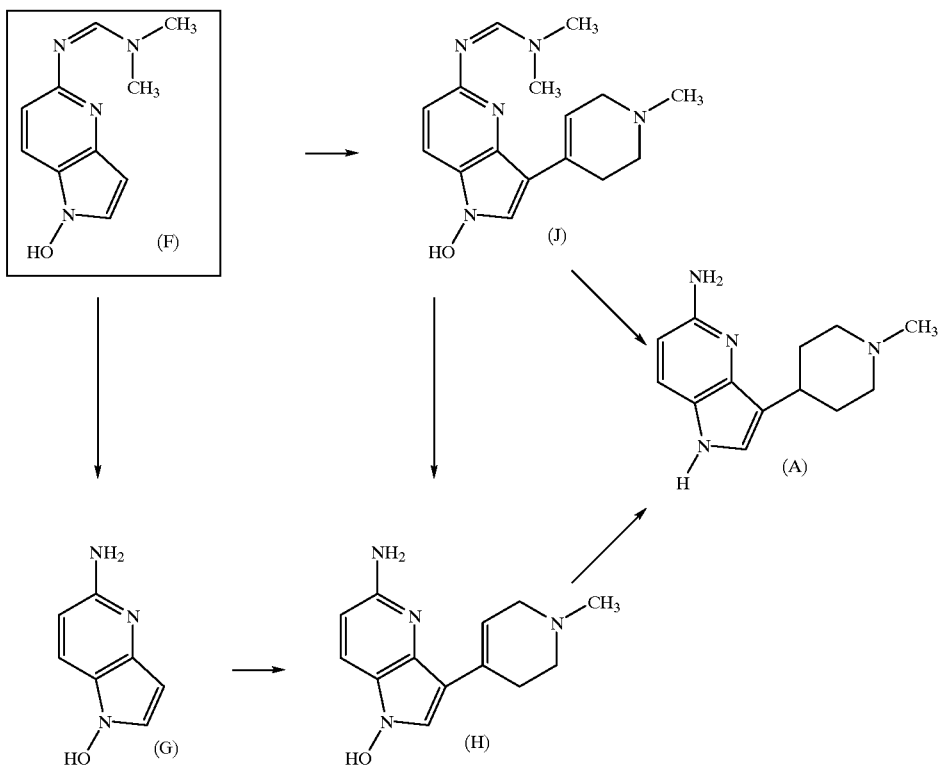

A solution of 1-hydroxy-5-(dimethylaminomethyleneimino)pyrrolo[3,2-b]pyridine (F) and 1-methyl-4-piperidinone in a suitable solvent is treated with an appropriate base to provide 1-hydroxy-3-(1-methyl-1,2,3,6-tetrahydropyridin-4-yl)-5-(dimethylaminomethyleneimino)pyrrolo[3,2-b]pyridine (J). Suitable solvents include the lower alkanols such as methanol, ethanol, propanol, isopropanol, and mixtures thereof. Preferred solvents are methanol, ethanol and mixtures thereof. Ethanol is an especially preferred solvent.

At least about one to about five equivalents of 1-methyl-4-piperidinone are added to the reaction mixture. Preferably about 2 to about 3 equivalents are added. It is especially preferred that about 3 equivalents of 1-methyl-4-piperidinone are added to the reaction mixture.

Appropriate bases are any base capable of facilitating the reaction without interfering with the formation of product. Appropriate bases include lithium, potassium, or sodium hydroxide, and amines. It is preferred that when the base is an amine it is a secondary dialkyl amine or a secondary cyclic amine. Secondary dialkyl amines include dimethylamine, diethylamine, methylethylamine and the like. Cyclic secondary amines include pyrrolidine, piperidine, piperazine, morpholine, and the like. A preferred base is a secondary amine, and dimethylamine is especially preferred.

The reaction mixture is agitated at about room temperature until the reaction is complete. After the reaction is complete the product is isolated by standard procedures, preferably by filtration or centrifugation.

Conversion of 1-hydroxy-3-(1-methyl-1,2,3,6-tetrahydropyridin-4-yl)-5-(dimethylaminomethyleneimino)-pyrrolo[3,2-b]pyridine (J) to 5-amino-3-(piperidin-4-yl)-pyrrolo[3,2-b]pyridine (A) is accomplished by hydrogenation in the presence of a precious metal catalyst. The substrate (J) is dissolved in a suitable solvent containing the precious metal catalyst. Suitable solvents include the lower alkanols such as methanol, ethanol, propanol and isopropanol. The preferred solvent is methanol. Precious metal catalysts are as described supra with 10% palladium on carbon preferred. The reaction mixture is hydrogenated at an initial pressure of from about 10 to about 50 p.s.i. Preferably the initial pressure is from about 30 to about 50 p.s.i. It is especially preferred that the initial pressure is about 50 p.s.i. The reaction mixture is hydrogenated at about ambient temperature. The product is isolated by standard isolation techniques.

The skilled artisan will appreciate that alternative processes for the preparation of 5-amino-3-(1-methylpiperidin-4-yl)pyrrolo[3,2-b]pyridine (A) are available by optionally modifying the 5-dimethylaminomethyleneimino moiety of compounds (F) or (J) to provide the corresponding 5-amino compounds (G) or (H) prior to subsequent reactions if desired. Compound (F) may be subjected to a refluxing lower alkanol, preferably methanol or ethanol, to provide 1-hydroxy-5-aminopyrrolo[3,2-b]pyridine (G). Compound (H), 1-hydroxy-3-(1,2,3,6-tetrahydropyridin-4-yl)-5-aminopyrrolo-[3,2-b]pyridine, may be prepared either by reacting (G) with 1-methyl-4-piperidinone under the conditions previously described, or by subjecting (J) to acidic hydrolysis conditions. Compound (H) is then converted to (A) by hydrogenation in water under the conditions described supra. It is preferred that the 5-dimethylaminomethyleneimino moiety of compounds (F) or (J) be converted to the corresponding amino moiety prior to hydrogenation to provide 5-amino-3-(1-methylpiperidin-4-yl)pyrrolo[3,2-b]pyridine (A).

The 1-hydroxypyrrolo[3,2-b]pyridines (F), (G), (H), and (J) are encompassed by Formula I:

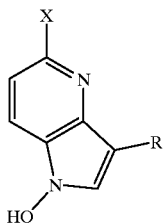

I where:
 X is amino or (CH$_3$)$_2$NCH=N—; and
 R is hydrogen or 1-methyl-1,2,3,4-tetrahydropyridin-4-yl; and acid addition salts thereof. The compounds of Formula I are novel and represent a further embodiment of the present invention.

The 5-HT$_{1F}$ agonist N-[propionyl]-5-amino-3-(1-methylpiperidin-4-yl)pyrrolo[3,2-b]pyridine is prepared by reacting the 5-aminopyrrolo[3,2-b]pyridine (A) with an appropriate propionyl chloride, bromide, iodide, or anhydride, optionally in the presence of an acylation catalyst such as dimethylaminopyridine, in the presence of a suitable base. Suitable bases include amines typically used as acid scavengers, such as pyridine or triethylamine, or commercially available polymer bound bases such as polyvinylpyridine. Alternatively, the reaction may be performed in pyridine, which serves as solvent and base. Typically, the product may be isolated by washing the reaction mixture with water and concentrating the remaining organics under reduced pressure. When an excess of acylating agent has been used, however, a polymer bound primary or secondary amine, such as an aminomethylated polystyrene, may be conveniently added to react with the excess reagent. Isolation of products from reactions where a polymer bound reagent has been used is greatly simplified, requiring only filtration of the reaction mixture and then concentration of the filtrate under reduced pressure. The product from these reactions may be purified chromatographically or recrystallized from a suitable solvent if desired. Under certain circumstances, diacylation of the 5-amino moiety may occur. Subjecting the diacylated product to either basic or acidic hydrolysis conditions at ambient temperature provides N-[propionyl]-5-amino-3-(1-methylpiperidin-4-yl)pyrrolo[3,2-b]pyridine.

The 5-aminopyrrolo[3,2-b]pyridine (A) may also be reacted with propanoic acid in the presence of typical peptide coupling reagents such as N,N'-carbonyldiimidazole (CDI), N,N'-dicyclohexylcarbodiimide (DCC) and 1-(3-dimethylaminopropyl)-3-ethylcarbodiimide hydrochloride (EDC). A polymer supported form of EDC has been described (*Tetrahedron Letters*, 34(48), 7685 (1993)) and is very useful for the preparation of N-[propionyl]-5-amino-3-(piperidin-4-yl)pyrrolo[3,2-b]piperidine, which is isolated and purified as previously described.

EXAMPLE 1

Mononitrated 6-amino-2-picoline 110 gm (1.02 mole) molten 6-amino-2-picoline were added dropwise to 500 mL concentrated sulfuric acid which had been precooled to −15° C. at rate to maintain the temperature of the sulfuric acid solution under 20° C. The solution was then cooled to about −6° C. and then a solution of 49 mL 90% nitric acid (1.16 mole) in 49 mL sulfuric acid precooled to about 0° C. was added dropwise over about 30 minutes, maintaining the temperature at about 0° C. The reaction mixture was stirred at about 0° C. for one hour and was then allowed to warm to about 10° C. over an hour. The temperature of the reaction mixture was maintained at about 10° C. for one hour and was then allowed to warm to about 20° C. over an hour. The reaction mixture was maintained at about 20° C. for 2 hours. The reaction mixture was poured into 8 L of ice with vigorous stirring. The reaction mixture was then adjusted to pH ~9 by the addition of 1.5 L concentrated ammonium hydroxide, maintaining the temperature of the reaction mixture at about 24° C. by the addition of ice as needed. The resulting slurry was filtered and the solid washed several times with water. The solid was dried at 70° C. under vacuum for 3 days to provide 135.4 gm (87%) of a 2:1 mixture of 3-nitro-:5-nitro-6-amino-2-picoline (B).

Sublimation 20 gm lots of the nitration mixture were sublimed twice under vacuum at 125° C. for 6 hours each. The 5-nitro isomer was sublimed as a bright yellow powder and discarded. The 3-nitro isomer which remained in the bottom of the sublimation apparatus was collected. A total of 121 gm were sublimed to provide 60.9 gm (75.5%) of the crude 3-nitro isomer. 58 gm of the crude 3-nitro isomer were slurried in 200 mL hot 95:5 ethanol:water. The mixture was cooled to room temperature and diluted with 200 mL of water. After two hours the precipitate was collected by filtration and rinsed several times with water. The solid was dried under vacuum at room temperature to provide 38 gm (65% based on 58 gm crude) 3-nitro-6-amino-2-picoline (C).

MS(m/e): 153 (M$^+$); Calculated for C$_6$H$_7$N$_3$O$_2$: Theory: C, 47.05; H, 4.61; N, 27.44. Found: C, 47.08; H, 4.53; N, 27.53.

Recrystallization

Alternatively, a mixture of 20 gm of the nitration mixture and 800 mL toluene were heated at reflux for 15 minutes. The mixture was filtered at 95° C. and the mother liquors allowed to cool to room temperature. After 4 hours the crystalline solid was collected, washed with 100 mL toluene, and dried under reduced pressure at 50° C. for 16 hours to provide 13.7 gm (68%) essentially pure 3-nitro-6-amino-2-picoline (C). m.p.=190.4° C.;

EXAMPLE 2

2-(2-dimethylaminoethen-1-yl)-3-nitro-6-(dimethylaminomethyleneimino)pyrrolo[3,2-b]pyridine (E)

A mixture of 60 gm (0.39 mole) 3-nitro-6-amino-2-picoline (C) in 260 mL dimethylformamide was treated with 260 mL (1.83 mole) 94% dimethylformamide dimethylacetal and the solution was heated at reflux for 48 hours. The reaction was concentrated under reduced pressure and the residual solid slurried with toluene. The toluene was evaporated under reduced pressure. This procedure was repeated 5 times. The final residue was slurried with 300 mL methyl tert-butyl ether and then filtered. This solid was washed 3 times with 300 mL methyl tert-butyl ether and the black solid was finally dried under reduced pressure to provide 90.6 gm (88%) of the desired compound.

MS(m/e): 263.1 (M$^+$); Calculated for C$_{12}$H$_{17}$N$_5$O$_2$: Theory: C, 54.74; H, 6.51; N, 26.60. Found: C, 54.84; H, 6.49; N, 26.79.

Isolation by Crystallization

A solution of 38.8 gm (0.25 mole) 3-nitro-6-amino-2-picoline (C) in 172 mL dimethylformamide was treated with 172 mL dimethylformamide dimethylacetal and the mixture was heated at about 97° C. for 42 hours. The reaction mixture was then cooled to room temperature and was diluted with 650 mL isopropanol. The reaction mixture was allowed to stand for 18 hours at room temperature and was then cooled to 3–5° C. with stirring for an additional 2 hours. The slurry was filtered, the solid washed 2×75 mL isopropanol, and dried under reduced pressure at 45° C. for 16 hours to provide 58.9 gm (88%,) of the title compound.

EXAMPLE 3

Alternate Synthesis of 2-(2-dimethylaminoethen-1-yl)-3-nitro-6-(dimethylaminomethyleneimino) pyrrolo[3,2-b]pyridine (E)

A mixture of 133 gm (0.86 mole) of mononitrated 6-amino-2-picoline (B) in 500 mL dimethylformamide was treated with 500 mL (3.5 mole) 94% dimethylformamide dimethylacetal and heated at reflux for 40 hours. After cooling to room temperature, the reaction mixture was divided in half and each half was poured into 10 L of water at 0° C. with vigorous stirring. After 10 minutes, the mixture was filtered and the solid was slurried/rinsed with 3×1 L of water. The solid was dried under vacuum at 65° C. for 2.5 days to provide 183 gm (81%) of the title compound as a red solid.

EXAMPLE 4

1-hydroxy-5-(dimethylaminomethylimino)pyrrolo-[3,2-b]pyridine (F) dihydrochloride A mixture of 23.4 gm (89 mMol) 2-(2-dimethylaminoethen-2-yl)-3-nitro-5-(dimethylaminomethyleneimino)pyrrolo[3,2-b]-pyridine (E) and 0.7 gm 10% palladium on carbon in 234 mL anhydrous methanol were treated with 140 mL 5.9 N ethanolic hydrogen chloride. The resulting mixture was hydrogenated for 1.5 hours under an initial hydrogen pressure of 30 p.s.i. The reaction was exothermic, reaching a temperature of 42° C. The reaction mixture was diluted with 585 mL ethanol and was stirred at room temperature for 1 hour at room temperature. The precipitate was filtered and rinsed with 50 mL ethanol. The solid was taken up in 1.1 L methanol, filtered, and then concentrated under reduced pressure. The residual solid was dried under reduced pressure to provide 20.5 gm (83%) of the desired compound (containing 5% 5-(dimethylaminomethyleneimino)pyrrolo [3,2-b]pyridine) as a yellow solid.

A 3.6 gm portion of the desired compound was suspended in 36 mL methanol followed successively by 90 mL anhydrous ethanol and 10.8 mL 5.9 N hydrogen chloride in ethanol. The mixture was stirred for 4 hours at room temperature and was then filtered and the solid washed with 2×5 mL ethanol. The resulting yellow solid was dried under reduced pressure at 45° C. to provide 3.39 gm (94.2%) of the title compound (containing 3% % 5-(dimethylaminomethyleneimino)pyrrolo[3,2-b]pyridine)

m.p.=213–4° C.; MS(m/e)=205 (M+1)

EXAMPLE 5

Alternate Procedure for the Preparation of 1-hydroxy-5-(dimethylaminomethylimino)pyrrolo[3,2-b]pyridine (F) dihydrochloride Beginning with 1.0 gm (3.8 mMol) 2-(2-dimethylaminoethen-2-yl)-3-nitro-5-(dimethylaminomethyleneimino)pyrrolo[3,2-b ]- pyridine (E), the reaction conditions of Example 4 were duplicated except that the reaction temperature was controlled such that it did not exceed 27° C. 0.95 gm (90%) of the title compound were recovered.

EXAMPLE 6

1-hydroxy-5-aminopyrrolo[3,2-b]pyridine (G) hydrochloride

A mixture of 0.06 gm 10% palladium on carbon, 2 gm (0.76 mMol) 1-hydroxy-5-(dimethylaminomethylimino) pyrrolo[3,2-b ]- pyridine (F) dihydrochloride, and 7.5 mL 9.1 N ethanolic hydrogen chloride in 40 mL methanol was subjected to catalytic hydrogenation for 1.5 hours at an initial hydrogen pressure of 10 p.s.i. Once the hydrogenation was complete, the reaction mixture was heated at 70° C. for three hours. The reaction mixture was cooled to room temperature and filtered. The residual solid was rinsed with methanol and the filtrate concentrated under reduced pressure. The residual solid was dried under vacuum at 50° C. for 6 hours to provide 2.64 gm (80%) of the title compound as a light brown solid. An analytical sample was recrystallized from ethanolic hydrogen chloride.

m.p.=227–8° C.; MS(m/e)=150 (M+1); Calculated for $C_7H_7N_3O$—HCl: Theory: C, 45.40; H, 4.32; N, 22.70; O, 8.65; Cl, 19.10. Found: C, 45.49; H, 4.26; N, 22.63; O, 8.47; Cl, 18.90.

EXAMPLE 7

1-hydroxy-5-(dimethylaminomethylimimo)-3-(1-methyl-1,2,3,6-tetrahydropyridin-4-yl)pyrrolo[3,2-b] pyridine (J)

A mixture of 13.5 gm (48.7 mMol) 1-hydroxy-5-(dimethylaminomethyleneimino)pyrrolo[3,2-b]pyridine (F) dihydrochloride and 17.5 gm (155 mMol) 1-methyl-4-piperidone in 270 mL anhydrous ethanol was stirred until homogeneous. At this point 19.4 mL (109 mMol) 5.6 N dimethylamine in ethanol were added and the reaction mixture stirred at room temperature for 4 hours. The yellow precipitate was filtered, washed 2×27 mL ethanol, and dried under reduced pressure at 45° C. to provide 13.4 gm (92%) of the desired compound as a yellow solid.

m.p.=212–3° C.; MS(m/e)=300 (M+1).

EXAMPLE 8

5-amino-3-(1-methylpiperidin-4-yl)pyrrolo[3,2-b] pyridine (A)

A mixture of 0.28 gm (0.94 mMol) 1-hydroxy-5-(dimethyl-aminomethyleneimimo)-3-(1-methyl-1,2,3,6-tetrahydropyridin-4-yl)pyrrolo[3,2-b]pyridine (J) and 0.10 gm 10% palladium on carbon in 20 mL methanol was hydrogenated for about 18 hours under an initial hydrogen pressure of 50 p.s.i. The reaction mixture was filtered and the filtrate concentrated under reduced pressure to provide 0.21 gm (96%) of the title compound.

EXAMPLE 9

1-hydroxy-5-amino-3-(1-methyl-1,2,3,6-tetrahydropyridin-4-yl)pyrrolo[3,2-b]pyridine (H) dihydrochloride A suspension of 0.85 gm (2.8 mMol) 1-hydroxy-5-(dimethylaminomethyleneimimo)-3-(1-methyl-1,2,3,6- tetrahydropyridin-4-yl)pyrrolo[3,2-b]pyridine (J) in 18 mL ethanol containing 1.2 mL (14.5 mMol) concentrated hydrochloric acid was heated to reflux for 7 hours. The reaction mixture was allowed to cool to room temperature and was then stirred for about 18 hours. The suspension was filtered, the solid washed 2×1.8 mL anhydrous ethanol, and then dried under reduced pressure at 45° C. to provide 0.84 gm (93%) of the title compound.

m.p.=282–3° C. (decomposition); MS(m/e)=245 (M+1); Calculated for $C_{13}H_{16}N_4O \cdot 2HCl$: Theory: C, 49.37; H, 5.70; N, 17.72; O, 5.06; Cl, 22.35. Found: C, 49.27; H, 5.71; N, 17.39; O, 5.38; Cl, 21.70.

EXAMPLE 10

Alternate Synthesis of 5-amino-3-(1-methylpiperidin-4-yl)pyrrolo[3,2-b]pyridine (A)

A suspension of 1 gm (3.15 mMol) 1-hydroxy-5-amino-3-(1-methyl-1,2,3,6-tetrahydropyridin-4-yl)pyrrolo[3,2-b]pyridine (H) dihydrochloride and 0.20 gm 10% palladium on carbon in 10 mL demineralized water was hydrogenated at ambient temperature with an initial hydrogen pressure of 45 p.s.i. After four hours the reaction mixture was filtered and the filtrate treated with 6 mL 2N aqueous sodium hydroxide. After the addition of 0.2 mL tetrahydrofuran the reaction mixture was stirred for 3 hours and the resulting precipitate collected by filtration. The solid was dried under reduced pressure at 50° C. to provide 0.59 gm (94%) of the title compound.

EXAMPLE 11

N-[propionyl]-5-amino-3-(1-methylpiperidin-4-yl) pyrrolo[3,2-b]piperidine

A suspension of 0.5 gm (2.17 mMol) 5-amino-3-(1-methyl-piperidin-4-yl)pyrrolo[3,2-b]pyridine (A) and 0.30 gm (2.27 mMol) propionic anhydride in 3.5 mL tetrahydrofuran was stirred at ambient temperature for about 18 hours. The reaction mixture then diluted with deminieralized water and the solution concentrated under reduced pressure to provide an aqueous residue weighing 7.5 gm. To this yellow solution were added successively 1.4 mL 2N aqueous sodium hydroxide and 1 mL tetrahydrofuran. The mixture was stirred for 3 hours at room temperature and the resulting suspension filtered. The solid was washed with 4 mL water and dried under reduced pressure at 55° C. to provide 0.59 gm (94%) of the title compound.

The ability of N-[propionyl]-5-amino-3-(1-methylpiperidin-4-yl)pyrrolo[3,2-b]pyridine to bind to the 5-$HT_{1F}$ receptor subtype was measured essentially as described in U.S. Pat. No. 5,521,196.

Membrane Preparation

Membranes were prepared from transfected Ltk- cells which were grown to 100% confluency. The cells were washed twice with phosphate-buffered saline, scraped from the culture dishes into 5 mL of ice-cold phosphate-buffered saline, and centrifuged at 200×g for 5 minutes at 4° C. The pellet was resuspended in 2.5 mL of ice-cold Tris buffer (20 mM Tris HCl, pH=7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The pellet resulting from this centrifugation was washed once in ice-cold Tris wash buffer and resuspended in a final buffer containing 50 mM Tris HCl and 0.5 mM EDTA, pH=7.4 at 23° C. Membrane preparations were kept on ice and utilized within two hours for the radioligand binding assays. Protein concentrations were determined by the method of Bradford (Anal. Biochem., 72, 248–254 (1976)).

Radioligand Binding

[$^3$H-5-HT] binding was performed using slight modifications of the 5-$HT_{1D}$ assay conditions reported by Herrick-Davis and Titeler (J. Neurochem., 50, 1624–1631 (1988)) with the omission of masking ligands. Radioligand binding studies were achieved at 37° C. in a total volume of 250 μL of buffer (50 mM Tris, 10 mM $MgCl_2$, 0.2 mM EDTA, 10 μM pargyline, 0.1% ascorbate, pH=7.4 at 37° C.) in 96 well microtiter plates. Saturation studies were conducted using [$^3$H]5-HT at 12 different concentrations ranging from 0.5 nM to 100 nM. Displacement studies were performed using 4.5–5.5 nM [$^3$H]5-HT. The binding profile of drugs in competition experiments was accomplished using 6–12 concentrations of compound. Incubation times were 30 minutes for both saturation and displacement studies based upon initial investigations which determined equilibrium binding conditions. Nonspecific binding was defined in the presence of 10 μM 5-HT. Binding was initiated by the addition of 50 μL membrane homogenates (10–20 μg). The reaction was terminated by rapid filtration through presoaked (0.5% poylethyleneimine) filters using 48R Cell Brandel Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [$^3$H]5-HT averaged between 45–50%. Binding data was analyzed by computer-assisted nonlinear regression analysis (Accufit and Accucomp, Lunden Software, Chagrin Falls, Ohio). $IC_{50}$ values were converted to $K_i$ values using the Cheng-Prusoff equation (Biochem. Pharmacol., 22, 3099–3108 (1973)). All experiments were performed in triplicate.

N-[propionyl]-5-amino-3-(1-methylpiperidin-4-yl)pyrrolo[3,2-b]pyridine was found to have affinity for the 5-$HT_{1F}$ receptor as measured by the procedure described supra.

As was reported by R. L. Weinshank, et al., WO93/14201, the 5-$HT_{1F}$ receptor is functionally coupled to a G-protein as measured by the ability of serotorin and serotonergic drugs to inhibit forskolin stimulated cAMP production in NIH3T3 cells transfected with the 5-$HT_{1F}$ receptor. Agonist activation of G-protein-coupled receptors also results in the release of GDP from the α-subunit of the G protein and the subsequent binding of GTP. The binding of the stable analog [$^{35}$S]GTPγS is an indicator of this receptor activation.

Membrane Preparation

Mouse LM(tk-)cells stably transfected with the human 5-$HT_{1F}$ receptor and grown in suspension were harvested by centrifugation, resuspended in 50 mM Tris-HCl, pH 7.4, in aliquots of 2×10$^8$ cells and frozen at −70° C. until the day of the assay. On the assay day, an aliquot of cells was thawed, resuspended in 35 mL of 50 mM Tris-HCl, pH 7.4, and centrifuged at 39,800×g for 10 minutes at 4° C. The resulting pellet was resuspended in 50 mM Tris-HCl, pH 7.4, incubated for 10 minutes at 37° C. and centrifuged at 39,800×g for 10 minutes at 4° C. The pellet was resuspended and centrifuged once more, with the final pellet being resuspended in 4 mM $MgCl_2$, 160 mM NaCl, 0.267 mM EGTA, 67 mM Tris-HCl, pH 7.4, such that a 200 μL aliquot contained contained approximately 15–25 μg protein.

[35S]GTPγS binding

All incubations were performed intriplicate in a total volume of 800 µL. Drug dilution in water, 200 µL, spanning 6 log units, was added to 400 µL of Tris-HCl, pH 7.4, containing 3 mM MgCl$_2$, 120 mM NaCl, 0.2 mM EGTA, 10 µM GDP, and 0.1 nM [35S]GTYγS. Membrane homogenate, 200 µL, was added and then the tubes were incubated for 30 minutes at 37° C. Using a Brandel cell harvester (model MB-48R, Brandel, Gaithersburg, Md.), the incubations were then terminated by vacuum filtration through Whatman GF/B filters which had been wet with water or 20 mM Na$_4$P$_2$O$_7$ and precooled with 4 mL of ice-cold 50 mM Tris-HCl, pH 7.4. The filters were then washed rapidly with 4 mL of ice-cold 50 mM Tris-HCl, pH 7.4. The amount of radioactivity captured on the filters was determined by liquid scintillation spectrometry using an LS6000IC (Beckman Instruments, Fullerton, Calif.). GTYγS, 10 µp, defined nonspecific binding. Protein was determined by the method of Bradford (*Anal. Biochem.*, 72, 248–254 (1976)).

Statistical Analysis

Efficacy values for test compounds were expressed as the percent binding relative to 10 µM 5-HT. Nonlinear regression analysis was performed on the concentration response curves using a four parameter logistic equation described by De Lean et al., (*Mol. Pharamacol.*, 21, 5–16 (1982)). Analysis of variance, followed by the Tukey-Kramer Honestly Significant Difference test (JMP; SAS Institute Inc., Cary, N.C.) was performed on the pEC$_{50}$ values and the E$_{max}$ values. N-[propionyl]-5-amino-3-(1-methylpiperidin-4-yl)pyrrolo[3,2-b]pyridine was found to be an agonist of the 5-HT$_{1F}$ receptor by the assay described supra.

We claim:

1. A process for the preparation of 5-amino-3-(1-methylpiperidin-4-yl)pyrrolo-[3,2-b]pyridine (A), comprising the steps of:
   i) condensing 1-hydroxy-5-(dimethylaminomethyleneimino)pyrrolo[3,2-b]pyridine (F) with 1-methyl-4-piperidinone in the presence of a base to provide 1-hydroxy-5-(dimethylaminomethyleneimino)-3-(1-methyl-1,2,3,6-tetrahydropyridin-4-yl)pyrrolo[3,2-b]pyridine (J);
   ii) optionally deprotecting (J) to provide 1-hydroxy-5-amino-3-(1-methyl-1,2,3,6-tetrahydropyridin-4-yl)pyrrolo-[3,2-b]pyridine (H); and
   iii) hydrogenating either (J) or (H).

2. The process of claim 1 where 1-hydroxy-5-(dimethylaminomethyleneimino)-3-(1-methyl-1,2,3,6-tetrahydropyridin-4-yl)pyrrolo[3,2-b]pyridine (J) is deprotected to provide 1-hydroxy-5-amino-3-(1-methyl-1,2,3,6-tetrahydropyridin-4-yl)pyrrolo-[3,2-b]pyridine (H).

3. A process for the preparation of 5-amino-3-(1-methylpiperidin-4-yl)pyrrolo[3,2-b]pyridine (A) comprising the steps of:
   i) condensing 1-hydroxy-5-aminopyrrolo[3,2-b]-pyridine (G) with 1-methyl-4-piperidinone in the presence of a base to provide 1-hydroxy-5-amino-3-(1-methyl-1,2,3,6-tetrahydropyridin-4-yl)pyrrolo[3,2-b]pyridine (H); and
   ii) hydrogenating (H).

4. A process for the preparation of 5-amino-3-(1-methylpiperidin-4-yl)pyrrolo[3,2-b]pyridine (A), comprising the steps of:
   i) nitrating 6-amino-2-picoline to provide a mononitrated 6-amino-2-picoline consisting of a mixture of 3-nitro- and 5-nitro-6-amino-2-picoline (B);
   ii) optionally separating the mixture of 3-nitro- and 5-nitro-6-amino picoline to provide a mononitrated 6-amino-2-picoline consisting of substantially pure 3-nitro-6-amino-2-picoline (C);
   iii) reacting a mononitrated 6-amino-2-picoline selected from (B) or (C) with a dimethylaminoformylating agent to provide 2-(2-dimethylaminoethen-1-yl)-3-nitro-6-(dimethylaminomethyleneimino)pyridine (E);
   iv) hydrogenating (E) in the presence of acid to provide 1-hydroxy-5-dimethylaminomethyleneiminopyrrolo[3,2-b]pyridine (F);
   v) reacting (F) with 1-methyl-4-piperidinone in the presence of a base to provide 1-hydroxy-5-(dimethylaminomethyleneimino)-3-(1-methyl-1,2,3,6-tetrahydropyridin-4-yl)pyrrolo[3,2-b]pyridine (J);
   vi) optionally deprotecting (J) to provide 1-hydroxy-5-amino-3-(1-methyl-1,2,3,6-tetrahydropyridin-4-yl)pyrrolo-[3,2-b]pyridine (H); and
   vii) hydrogenating either (J) or (H).

5. The process of claim 4 where the mononitrated 6-amino-2-picoline is substantially pure 3-nitro-6-amino-2-picoline (C).

6. The process of claim 4 where (H) is hydrogenated in step vii).

7. The process of claim 5 where (H) is hydrogenated in step vii).

8. A process of claim 1, further comprising the step of acylating 5-amino-3-(1-methylpiperidin-4-yl)pyrrolo[3,2-b]pyridine (A) to provide N-[propionyl]-5-amino-3-(1-methylpiperidin-4-yl)pyrrolo[3,2-b]pyridine.

9. A process of claim 2, further comprising the step of acylating 5-amino-3-(1-methylpiperidin-4-yl)pyrrolo[3,2-b]pyridine (A) to provide N-[propionyl]-5-amino-3-(1-methylpiperidin-4-yl)pyrrolo[3,2-b]pyridine.

10. A process of claim 3, further comprising the step of acylating 5-amino-3-(1-methylpiperidin-4-yl)pyrrolo[3,2-b]pyridine (A) to provide N-[propionyl]-5-amino-3-(1-methylpiperidin-4-yl)pyrrolo[3,2-b]pyridine.

11. A process of claim 4, further comprising the step of acylating 5-amino-3-(1-methylpiperidin-4-yl)pyrrolo[3,2-b]pyridine (A) to provide N-[propionyl]-5-amino-3-(1-methylpiperidin-4-yl)pyrrolo[3,2-b]pyridine.

12. A process of claim 5, further comprising the step of acylating 5-amino-3-(1-methylpiperidin-4-yl)pyrrolo[3,2-b]pyridine (A) to provide N-[propionyl]-5-amino-3-(1-methylpiperidin-4-yl)pyrrolo[3,2-b]pyridine.

13. A process of claim 6, further comprising the step of acylating 5-amino-3-(1-methylpiperidin-4-yl)pyrrolo[3,2-b]pyridine (A) to provide N-[propionyl]-5-amino-3-(1-methylpiperidin-4-yl)pyrrolo[3,2-b]pyridine.

14. A process of claim 7, further comprising the step of acylating 5-amino-3-(1-methylpiperidin-4-yl)pyrrolo[3,2-b]pyridine (A) to provide N-[propionyl]-5-amino-3-(1-methylpiperidin-4-yl)pyrrolo[3,2-b]pyridine.

15. A process for the preparation of 1-hydroxy-5-dimethylaminomethyleneiminopyrrolo[3,2-b]pyridine (F), comprising the steps of:
   i) nitrating 6-amino-2-picoline to provide a mononitrated 6-amino-2-picoline consisting of a mixture of 3-nitro- and 5-nitro-6-amino-2-picoline (B);
   ii) optionally separating the mixture of 3-nitro- and 5-nitro-6-amino picoline to provide a mononitrated 6-amino-2-picoline consisting of substantially pure 3-nitro-6-amino-2-picoline (C);
   iii) reacting a mononitrated 6-amino-2-picoline selected from (B) or (C) with a dimethylaminoformylating agent to provide 2-(2-dimethylaminoethen-1-yl)-3-nitro-6-(dimethylaminomethyleneimino)pyridine (E);

iv) hydrogenating (E) in the presence of acid.

16. A 1-hydroxypyrrolo[3,2-b]pyridine of Formula I:

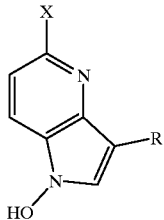

I where:

X is amino or $(CH_3)_2NCH{=}N{-}$; and

R is hydrogen or 1-methyl-1,2,3,6-tetrahydropyridin-4-yl; or an acid addition salt thereof.

17. A compound of claim 16 where X is amino.
18. A compound of claim 16 where R is hydrogen.
19. The compound of claim 17 where R is hydrogen.
20. A compound of claim 16 where R is 1-methyl-1,2,3,6-tetrahydropyridin-4-yl.
21. The compound of claim 17 where R is 1-methyl-1,2,3,6-tetrahydropyridin-4-yl.

* * * * *